Figure 1:
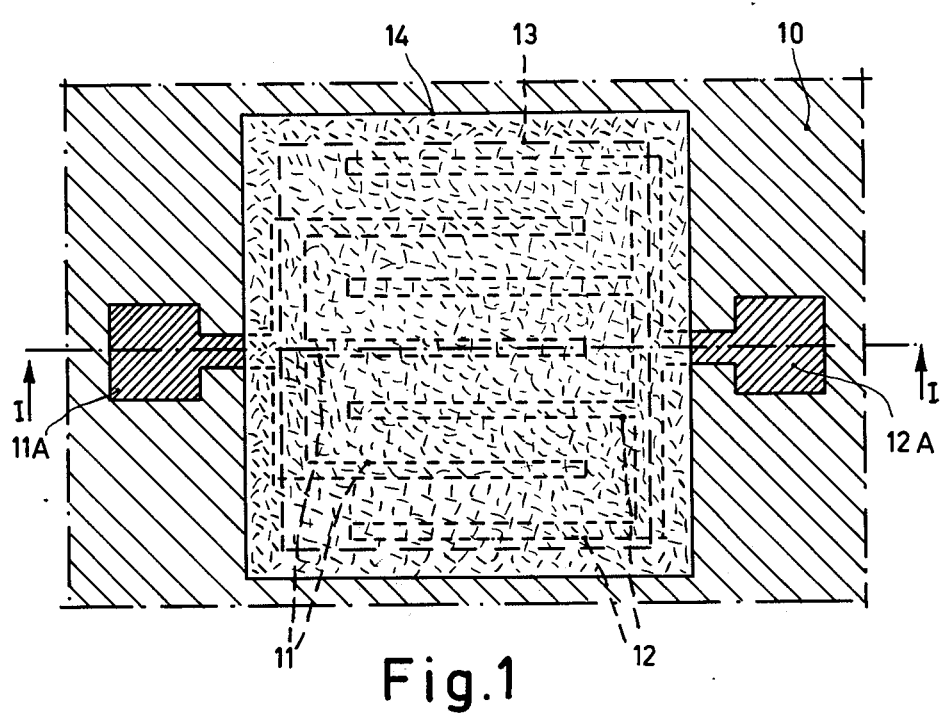

United States Patent [19]

Pompei et al.

[11] 4,025,892

[45] May 24, 1977

[54] PROBE FOR DETECTING GASEOUS POLAR MOLECULES SUCH AS WATER VAPOR

[75] Inventors: Jean Pompei, Noisy-le-Roi; Bernard Lacroix, Paris; Francis Pierrot, Rueil-Malmaison, all of France

[73] Assignee: U.S. Philips Corporation, New York, N.Y.

[22] Filed: May 13, 1975

[21] Appl. No.: 577,068

[30] Foreign Application Priority Data

May 27, 1974 France .............................. 74.18213

[52] U.S. Cl. ............................... 338/35; 200/61.06
[51] Int. Cl.² ........................................... H01L 7/00

[58] Field of Search ............. 338/34, 35; 23/232 E, 23/254 E, 255 E; 427/82, 88, 91, 93, 107; 340/235, 237; 200/61.04, 61.06; 73/23

[56] References Cited

UNITED STATES PATENTS

| 3,242,007 | 3/1966 | Jensen ................................. 427/93 |
| 3,864,659 | 2/1975 | Furuuchi et al. ..................... 338/35 |

Primary Examiner—C. L. Albritton
Attorney, Agent, or Firm—Frank R. Trifari

[57] ABSTRACT

Probe for selectively detecting polar molecules in a gaseous atmosphere in contact with the probe, characterized by a layer of semiconductor material covered by a film of dielectric material.

6 Claims, 4 Drawing Figures

PROBE FOR DETECTING GASEOUS POLAR MOLECULES SUCH AS WATER VAPOR

The invention relates to a probe for selectively detecting at least one constituent of a gaseous mixture in contact with the probe, the operation of this probe being based on the variation of its electrical resistance due to a reaction at the surface of the probe.

The invention relates in particular to the detection of polar electropositive or polar electronegative molecules. The terms "polar electropositive and polar electronegative molecules" are used herein to mean molecules which can produce positive or negative electric charges respectively on the surface of dielectrics on which the said molecules are held by adsorption forces. Such molecules are, for example, water molecules (electropositive) and oxygen molecules (electronegative).

The invention relates, by way of example, to a probe for detecting humidity.

The operation of various gas and vapor detectors in present use is based on variations of the electrical resistance or of the impedance of probes in the form of a layer or of a porous body consisting of a substance which is sensitive to a given gaseous or vaporous component and generally is a metal oxide or a mixture of metal oxides.

Such detectors for polar molecules, in particular humidity detectors, have two important disadvantages: their sensitivity is low and in addition it varies with time due to the facts that the quality of the probe electrodes deteriorates progressively due to electrolysis phenomena and that the active probe surface area decreases by contamination.

An improved humidity detector the operation of which is based on a principle completely different from that of the conventional detectors is described in French Patent Specification No. 2,160,095 according to which the detector comprises a semiconductor substrate which consists of silicon, germanium or gallium arsenide and a major surface of which is partly covered with a layer of stannic oxide ($SnO_2$). The remainder of the said surface is covered with a layer of silica ($SiO_2$) which serves to stabilize the characteristic of the semiconductor. Metal electrodes are applied to both major surfaces of the substrate, one on the stannic oxide layer and the other on the semiconductor surface.

It is stated that the said device forms a Schottky junction between the stannic oxide layer and the semiconductor substrate which is particularly sensitive to variations in the ambient humidity.

Such a device is a considerable improvement on prior devices, but has serious disadvantages: its response is slow (15 seconds elapse before a response is obtained to a change in relative humidity from 100% to about 0%) and also the slope of the characteristic of the Schottky diode as a function of relative humidity is steep, so that detection and measurements are inaccurate; this inaccuracy is increased by the small area of contact of the sensitive region of the diode with the ambient atmosphere, and furthermore the device consumes comparatively much energy for measuring low humidities, with consequent heating of the device to a temperature higher than the ambient temperature, which affects the measurements.

The invention obviates the aforementioned disadvantages of the known detectors.

It is an object of the present invention to provide a detector probe, particularly a probe for a detector of polar molecules, in particular a probe for a humidity detector, which is constructed so that due to the presence of a gaseous or vaporous constituent in a gaseous mixture the electrical resistance of the probe assumes a stable reproducible and correct value which moreover is reached after a very short time.

With respect to humidity detectors it is an object of the invention to provide either devices with threshold sensitivity of the mist detector type or devices of continuous sensitivity of the hygrometer type which can be used in monitoring systems.

According to the invention a probe for selectively detecting at least one constituent of a gaseous mixture in contact with the probe, the operation of this probe being based on the variation of its electrical resistance due to a reaction at the surface of the probe, is characterized in that it comprises a substrate provided with a layer of a semi-conductor material of thickness 0.05 to 0.08 $\mu$m to which are connected at least two electrodes and which is covered by a layer of a dielectric material of thickness 0.01 to 0.04 $\mu$m at least part of which is active as a detection area.

The dielectric layer serves to collect the particles of the gas to be detected. These particles, which may be electropositive or electronegative, together produce an electric charge when they are deposited on, and adhere to, the dielectric layer. Through the dielectric layer the electric charge induces capacitively a charge of opposite sign at the interface between the dielectric layer and the semiconductor layer. This results in a change of the charge initially stored at the interface (this charge is reduced or increased in accordance with the electric polarity of the particles of the detected gas) with a consequent change in the electrical resistance of the surface regions of the underlying semiconductor layer. The effect is stronger as the density of the charges in the collecting layer is higher.

The phenomenon probably is more complicated than the above explanation suggests and hence we do not wish to bind the invention to this explanation. In particular, the dielectric film acts by its nature, by its structure and mainly by the condition of its surface and by its thickness, and hence it is difficult to determine the proper function of each parameter in every possible case.

Compared with the probes of the known detectors the probe according to the invention has many advantages. First, the probe according to the invention is highly sensitive. If, for example, the probe is used as a mist detector the formation of a dense and opaque layer of water is preceded by a rapid and considerable reduction of the resistance of the probe. Thus a control device which may be connected to the probe can become operative as soon as the first microdrops are formed.

On the other hand, the detecting area which is in contact with the ambient atmosphere is very large with respect to the probe size, and this partly explains the high sensitivity of the probe.

The sensitivity of the probe is also influenced by the small thickness of the active elements which are in the form of thin films.

The probe according to the invention has the further advantage that in the inoperative condition, i.e. in the absence of gas or vapor molecules on the detection area or when the density of the said molecules is less than the alarm threshold for the probe, its consumption is very small and substantially negligible (about 1 microampere at 4 to 5 volts). This small consumption is related to the electrical resistance in the inoperative condition of the semiconductor layer, which resistance may be very large (several hundreds of kilo. ohms to several megohms, depending on the manufacturing conditions). As a result the probe is substantially not heated and remains at the ambient temperature, whch ensures correct detection.

Another important advantage of the probe according to the invention is that many suitable materials are available. By combining a given semiconductor material with a given dielectric material a probe can be constructed which has a specific sensitivity for a given constituent.

The possibility of obtaining a large number of combinations of semiconductor material and material of the dielectric layer is offered by the method of providing the said layers, which method is a technique of deposition in an ionized gaseous medium.

The term "deposition technique in an ionized gaseous medium" as used herein is to be understood to mean a plurality of possible techniques of deposition by means of a luminescent discharge maintained between at least two electrodes one of which is polarized with respect to the other.

This method of deposition which is especially performed for obtaining devices which mainly comprise a semiconductor layer covered by a dielectric layer is the subject of our copending French Patent Application No. 74-18214.

In a probe according to the invention suitable for detecting polar molecules the semiconductor layer may consist, for example, of a binary compound or a mixture of binary compounds of a metal and a metalloid. Preferably the semiconductor layer consists of zinc oxide. This layer is obtained by cathode sputtering of a zinc target in an oxidizing atmosphere. By the special discharge conditions, which will be described more fully hereinafter, a zinc oxide layer is obtained which when inoperative has a high electrical resistance (of the order of several megohms between the two conductive electrodes connected to this film). The said layer has n-type conductivity, because it is obtained by cathode sputtering; this will also be the case for a layer consisting of another material, in particular a layer consisting of another metal oxide or a layer of another binary compound, such as cadmium sulphide.

Advantageously the dielectric layer of the probe consists of an organo-metallic compound, for example a metal alcoholate or tetraethoxysilane or of polytetrafluoroethylene. The tetraethoxysilane layer is obtained by polycondensation of this substance in monomeric form in the atmosphere of a luminescent discharge. The polytetrafluoroethylene layer is obtained by cathode sputtering of a solid target of polytetrafluoroethylene.

During the entire process of deposition of the semiconductor layer and of the dielectric layer according to the method as described in the abovementioned French Patent Application the structure must remain insulated in the discharge so that the surfaces of the layers are continually at a floating potential equal to the potential of the discharge plasma.

We have found that the sensitivity range, the selectivity, the accuracy and the reliability of the probes according to the invention can be improved by suitable aftertreatments. The said aftertreatments mainly consist in that the surface of the dielectric layer is aftertreated by heating, by bombardment or by glow discharge. The thermal aftertreatment changes the density of the storage layer at the interface between the semiconductor layer and the dielectric film and also the distribution of the dipoles internally of the layer. Hence the said aftertreatments can be used for adjusting the electrical resistance of the probe. Bombardment and glow discharge have the same function as thermal aftertreatment and in addition change the surface texture of the dielectric film; thus they exert a certain influence on the absorption and desorption capacities of the said film and thus enable the threshold or the limits of operation of the probes to be set.

It should, however, be pointed out that the characteristics of the probes according to the invention are highly dependent upon the nature of the dielectric film.

A detector having threshold sensitivity is obtained by means of a probe which is used, for example, for detecting atmospheric humidity and the semiconductor layer of which consists of a binary compound and is covered by a dielectric film of polytetrafluoroethylene. Polytetrafluoroethylene is a hydrophobic substance on which the water vapor molecules cannot be retained by adsorption. Consequently the electric condition of the probe can only be influenced by humidity when water condenses on the surface of the said film. At this instant the initially high probe resistance is abruptly reduced. In this case the threshold value is strictly defined and corresponds to the saturation pressure of water vapor in the atmosphere monitored at a given temperature and a given pressure of this atmosphere.

A detector having continuous sensitivity is preferably obtained by means of a probe which is also used for detecting the humidity in the atmosphere and the semiconductor layer of which, which also consists of a binary compound, is coated with a film of polycondensed tetraethoxysilane. The said tetraethoxysilane is a hydrophilic substance on which the water molecules settle by sorption; hence in this case a continuous decrease of the resistance of the probe in accordance with the relative humidity of the ambient atmosphere is recorded.

We have, however, found that obtaining reliable measurements under equal conditions of relative humidity depends upon a bombardment to which the dielectric film is subjected after deposition. The bombardment is advantageously effected in an oxygen atmosphere; as an alternative, argon may be used. By the said bombardment a monomolecular layer of monometric tetraethoxysilane is removed which is deposited on the underlying region of polycondensed tetraethoxysilane on termination of the discharge during deposition of the dielectric film. This monomolecular layer adversely affects the regularity of detection.

If the probe is subjected to a thermal aftertreatment under suitable conditions instead of to a bombardment of the dielectric film in an oxygen or argon atmosphere, the probe will provide satisfactory measurements in a detector having threshold sensitivity. In this case the resistance of the probe remains comparatively high, and this resistance decreases progressively until the humidity of the atmosphere being monitored reaches a threshold beyond which the resistance drops abruptly.

In various embodiments of probes according to the invention used either in detectors having threshold sensitivity or in detectors having continuous sensitivity the response time is less than one second. Furthermore experience attained by extensive measurements has shown that under equal operational conditions the measurements of such probes are highly stable.

Figure 2:
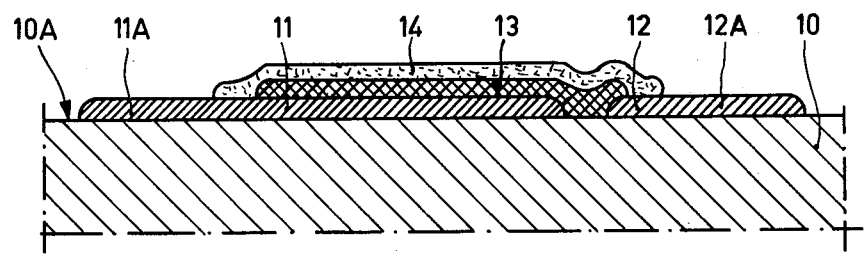
Figure 3:
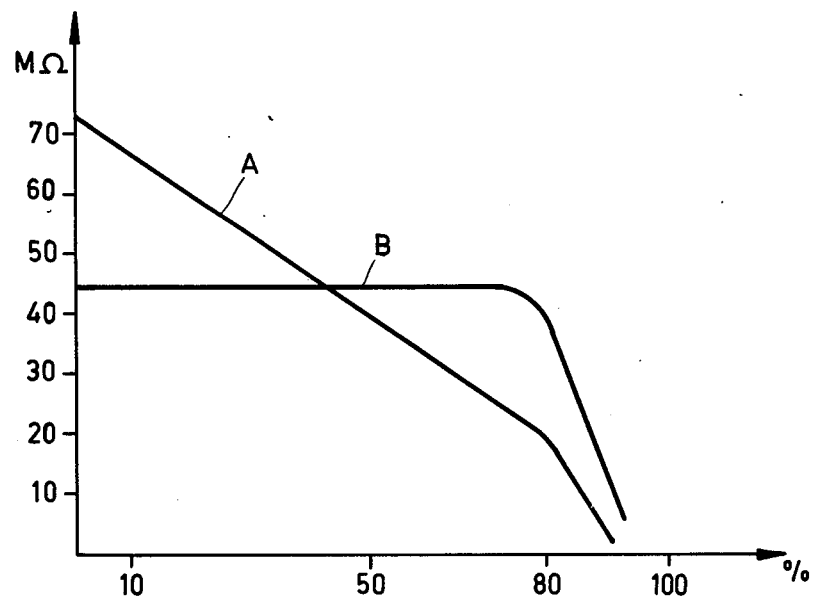
Figure 4:
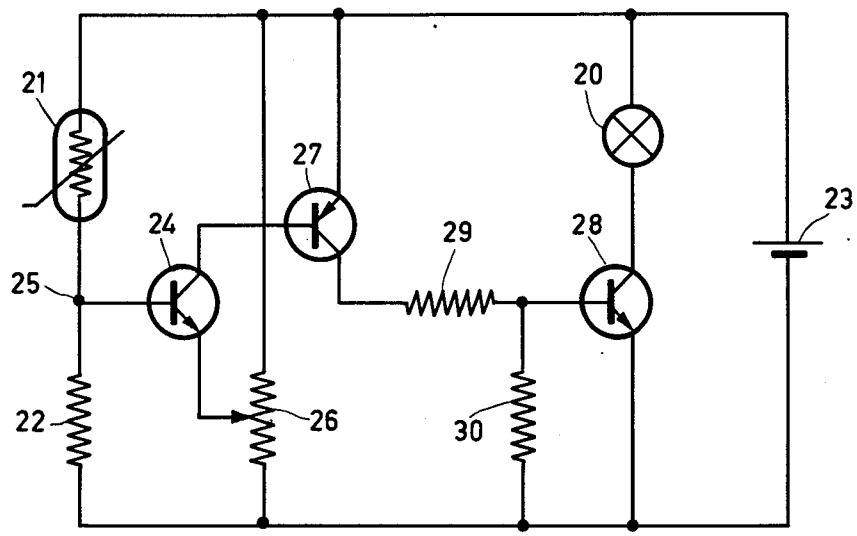

An embodiment of the invention will now be described, by way of example, with reference to the accompanying diagrammatic drawings, in which:

FIG. 1 is a top plan view of a probe for a mist detector according to the invention, FIG. 2 is a cross-sectional view thereof taken on the line I—I in FIG. 1, FIG. 3 is a graph which at a constant temperature shows the electrical resistance as a function of humidity of two probes according to the invention which have equal semiconductor layers but different dielectric films, and FIG. 4 is the circuit diagram of an amplifier including a probe according to the invention.

Referring now to the FIGURES, the probe according to the invention is realized on a solid dielectric substrate 10. The term "solid" has a relative meaning which should be judged in comparison with the usual thicknesses of the probe elements; it may be a thin strip, for example of glass, or a wafer the thickness of which corresponds to that of a glass pane.

On a major surface 10 A of the substrate 10 two thin semiconductor areas 11 and 12 are formed; these areas may have the form of interdigitated combs and constitute the electrodes of the probe. The two areas 11 and 12 may be a composite layer which comprises a nickel-chromium-nickel film and a gold film.

The areas 11 and 12 (with the exception of connecting pads 11A and 12A) and the surrounding parts of the substrate 10 are covered by a layer 13 of a semiconductor material, for example zinc oxide. The layer 13 is covered by a film 14 of a dielectric material, for example tetraethoxysilane or polytetrafluoroethylene, the surface of which constitutes the detection area of the probe.

The film 14 occupies a surface area of about 50 mm$^2$ on the substrate 10. The thickness of the conductive areas 11 and 12 is about 0.3 $\mu$m (from 0.2 to 0.4 $\mu$m), that of the semiconductive layer 13 about 0.06 $\mu$m (from 0.05 to 0.08 $\mu$m) and that of the dielectric film 14 about 0.02 $\mu$m (from 0.01 to 0.04 $\mu$m) in the case both of tetraethoxysilane and of polytetrafluoroethylene.

The layer 13 and the film 14 are obtained by a deposition technique in an ionized gaseous atmosphere as described in the aforementioned French Patent Application.

The thin layer of the areas 11 and 12 may be obtained in known manner by cathode sputtering, be deposition from vapor in a vacuum, by electrolysis or by a combination of these techniques.

The layer of nickel-chromium-nickel is obtained, for example, by vaporizing a nickel-chromium-nickel wire (80% nickel and 20% chromium) in a vacuum. The layer then is chemically etched to produce the desired configuration for the areas 11 and 12, and subsequently gold is applied by electrolysis.

The substrate 10 provided with the areas 11 and 12 then is placed on an aluminium collecting electrode of a cathode sputtering device having diode configuration the target of which is a plate of nickel-plated steel which carries the target proper of solid or powdered zinc which is arranged opposite the said collecting electrode.

The spacing between the target and the collecting electrode is 80 mm (from 50 to 90mm).

The discharge takes place in a dry air atmosphere the pressure of which is maintained at $0.5 \cdot 10^{-2}$ Torr (from $10^{-3}$ to $10^{-2}$ Torr). The supply voltage is a direct voltage of 2.5 kV (from 2 to 3 kV).

Under these conditions a discharge current of 1.60 mA (from 1.40 to 1.80 mA) is obtained per square cm of the target and a zinc oxide film 13 having stable oxygen vacancies is deposited on the substrate at a rate of 0.008 $\mu$m/minute (from 0.006 $\mu$m to 0.01 $\mu$m/minute).

The layer 13 is then covered by a dielectric layer of tetraethoxysilane under the following conditions; the assembly remains arranged on the collecting electrode of a cathode sputtering device of diode configuration the target of which is an aluminum plate. After a suitable vacuum has been produced in the sputtering space, a gas mixture is introduced which comprises 6 to 10% (preferably 8%) by volume of tetraethoxysilane and from 90 to 94% by volume of oxygen.

The pressure of the gas mixture in the space is adjusted to between $10^{-1}$ and $10^{-2}$ Torr, after which a glow discharge is produced between the target and the collecting electrode which causes the tetraethoxysilane to evaporate, the product of evaporation depositing in particular on the zinc oxide layer 13.

The choice of the spacing between the target and the collecting electrode is of high importance. If this spacing is small (of the order of 50 to 60 mm, as is usual for cathode sputtering operations), the deposited compound is exposed to an excessive ion and electron bombardment so that the ions and electrons will change the texture of the deposit and adversely affect its properties.

In the present case it was found that the spacing between the collecting electrode and the target must be at least 150 mm (between 150 and 200 mm). The voltage set up between the said electrodes is a direct voltage of 1.5 kV (from 1.4 to 1.6 kV). Under these conditions the strength of the discharge current is 1.5 mA (from 1 to 2mA) per square cm of the surface area of the target or collecting electrode.

The rate of growth of the polycondensed film 14 is 0.002 $\mu$m/minute (from 0.001 to 0.003 $\mu$m/minute).

When the dielectric film is to consist of polytetrafluoroethylene, a solid target of polytetrafluoroethylene is exposed to a bombardment in an argon atmosphere in known manner. The conditions under which deposition is effected are for example: the two electrodes, one of which supports the target while the other supports the body to be covered, are made of aluminium and are spaced from one another by a distance of 50 mm (from 40 to 60 mm). The pressure in the space is stabilized at 0.8 Torr (from 0.6 to 0.9 Torr). An alternating-voltage signal at a frequency of 13 MHz is applied to the target, and the high-frequency power used is 200 watts. The growth rate of the polytetrafluoroethylene film then is 0.003 $\mu$um/minute (from 0.002 to 0.005 $\mu$um/minute).

The complementary treatments to which the finished probe is subjected may vary, as described hereinbefore.

For a probe of zinc oxide covered by a tetraethoxysilane film and to be used as a detection element having threshold sensitivity for monitoring humidity in a given atmosphere, for example, the probe must be subjected to a thermal aftertreatment after being removed from the cathode sputtering space. This treatment is preferably performed in air for about 30 minutes (from 25 to 35 minutes) at a temperature of about 350° C (from 340° to 360° C). Taking into account the aforementioned conditions of deposition of the various layers, the said probe then in the inoperative condition has a high resistance of the order of several megohms or even tens of megohms which obviously depends upon the specific dimensions of the embodiment concerned.

If the probe comprising zinc oxide coated with tetraethoxysilane is to be used as an element for detecting humidity with continuous sensitivity, which requires the probe to be reliable in a resistance range and not for a single threshold value, the probe is exposed to a bombardment in an oxygen atmosphere carried out immediately after the deposition of the film 14. For this purpose the bombardment is effected in the space in which the film 14 is produced, the conditions of the bombardment being the same as those of the deposition, except that the atmosphere in which the discharge takes place consists of oxygen only. Thus after the deposition of the film 14 only the discharge gas has to be replaced. The bombardment in the pure oxygen atmosphere has a duration of three minutes (from 1 to 5 minutes) and after this time the monomolecular layer of monomeric tetraethoxysilane by which the underlying polycondensed tetraethoxysilane was covered on termination of the deposition of the film 14 has been removed.

In the case of a probe comprising zinc oxide coated with a film of polytetrafluoroethylene, which probe can also be used as a detection element having a sensitivity threshold, for example for monitoring humidity in an atmosphere, the probe is subjected to a thermal aftertreatment after the deposition of the film 14. Advantageously the conditions for carrying out this treatment are as follows. The atmosphere is air at normal atmospheric pressure, the temperature is 200° C (from 190° to 210° C) and the duration of the treatment is 60 minutes (from 55 to 65 minutes). After the thermal treatment the probe in the inoperative condition has a high resistance of several megohms.

The graph of FIG. 3 shows the electrical resistance characteristics as a function of the humidity of air at a temperature of 20° C for two high-resistance probes of equal size the semiconductor layers 13 of which are two comparable zinc oxide layers one of which is coated with a tetraethoxysilane film 14 (curve A) while the other is coated with a film 14 of polytetrafluoroethylene (curve B). The probes are fed with a direct current.

The graph, which is given by way of example only, shows that the behavior of a probe according to the invention is greatly dependent upon the nature of the dielectric layer the outer surface of which forms the detection area of the probe and also upon the aftertreatment to which the probe is subjected after the provision of the layer 13 and the dielectric film 14.

The probe to which curve A relates (zinc oxide and tetraethoxysilane) was subjected to ion bombardment in an oxygen atmosphere under the aforementioned conditions. Its resistance, which is very high in a dry air atmosphere, decreases linearly with increase of the humidity of the monitored atmosphere. This probe can advantageously be used as a sensitive element of a detector having continuous sensitivity. Beyond a humidity of about 80% the resistance decreases at a higher rate than below this value. This ultimately accelerated decrease of the resistance can be enhanced if the probe is not subjected to a bombardment but to a thermal aftertreatment; in this case it may be used for a detector having threshold sensitivity.

The probe to which curve B relates (zinc oxide and polytetrafluoroethylene) was subjected to a thermal aftertreatment. It was found that the resistance of the probe remains high and stable up to a humidity of about 75%, beyond which it decreases abruptly. Hence such a probe is highly suited for use in a humidity detector having a threshold.

The two examples of probes constituted by zinc oxide layers and dielectric films of tetraethoxysilane or polytetrafluoroethylene do not constitute a limitation of the invention. The zinc oxide layer may be replaced by a layer of another semiconductive oxide, for example, stannic oxide ($SnO_2$) or titanium oxide ($TiO_2$).

In any case, the constituent elements, the conditions of deposition of the layer 13, the dielectric film 14 and the aftertreatments must be chosen so as to be in accordance with the nature of the substances to be detected and for a given substance moreover in accordance with the sensitivity range to be covered. For a given substance to be detected a low-resistance probe, a medium-resistance probe or a high-resistance probe may be required.

Due to the high flexibility of the method of manufacturing the probes (multiplicity of the parameters in the cathode sputtering process, various characteristics of the thermal treatment or of the ion bombardment of the dielectric layer) the said method can readily satisfy the various typical requirements of the desired use. For example, we have made detectors for measuring air humidity which are provided with probes which are fed with alternating current and the resistance of which in the inoperative condition is about $10^6$ ohms and remains at this level for a humidity from 0 to 50% and then exponentially drops to $10^{-3}$ ohms for a rise in humidity from 50 to 80%. Conversely the probe resistance increases with reduction of humidity. It should be noted that the increase and decrease curves of the resistance completely coincide. Such probes may advantageously be used for automatic control of air conditioning or drying systems.

It should be mentioned that in all uses of probes according to the invention, in particular for detecting polar molecules and especially for detecting humidity, the probes may be fed with direct current or with alternating current.

The amplifier the circuit diagram of which is shown in FIG. 4 can be used in conjunction with a probe according to the invention, for example for a threshold sensitivity detector of the mist detector type. It is constructed so as to ignite an electric filament lamp or a signalling glowlamp 20 when a mist layer is formed on the detection area of the probe symbolically represented by a resistor 21. In the said amplifier the resistor 21 is connected in series with a fixed resistor 22 between the terminals of a supply source 23. The resistor 21 is connected to the positive terminal and the resistor 22 to the negative terminal. The base of an npn transistor 24 is connected to the junction point 25 of the resistors 21 and 22. The emitter of the transistor 24 is connected to the slider of a potentiometer 26 also connected between the terminals of the source 23. The collector of the transistor 24 is directly connected to the base of a pnp transistor 27 the emitter of which is connected to the positive terminal of the source 23, while the collector is connected to the base of an npn transistor 28 via a resistor 29. A resistor 30 may be included between the base of the transistor 28 and the negative terminal of the source 23 and serves as a leak resistor. The emitter of the transistor 28 is connected to the negative terminal of the source 23 and its collector is connected to a terminal of the lamp 20 the other terminal of which is connected to the positive terminal of the source 23.

The said amplifier is of a conventional type with continuous coupling between the various stages and hence its operation need not be described in more detail.

It should be mentioned that the emitter bias of the transistor 24 is adjusted by means of the potentiometer 26 in a manner such that the transistor 24 is cut off at the inoperative value of the resistor 21 (i.e. in the absence of mist on the probe represented by this resistor 21). Because the transistor 24 is cut off, the transistors 27 and 28 are also cut off; as a result the lamp 22 is extinguished.

When the value of the resistor 21 is reduced by condensation of mist, the potential of the junction point 25 becomes more positive so that the transistor 24 becomes conducting. The transistors 27 and 28 are successively rendered conductive and as a result a current traverses the lamp 22 which consequently emits light.

An amplifier for a mist detector of the type described may comprise the following components:

| | |
|---|---|
| Transistors 24 and 28 | BC 109 |
| Transistor 27 | BC 179 |
| Resistance 21 of the probe | 5 to 10 megohms in the inoperative condition and less than 1 megohm in the presence of mist |
| Resistor 22 | about 4 megohms |
| Potentiometer 26 | overall resistance 20 kilo-ohms, resistor 29 3 kilo-ohms and resistor 30 150 kilo-ohms |
| Lamp 20 | current strength 50 mA. |
| Voltage supplied by the source 23 | 4 to 4.5 volts. |

The above described amplifier does not mean a limitation of the invention. Nevertheless such a circuit is interesting because of the fact that in the inoperative condition its consumption is very small (restricted to the consumption of the potentiometer 26) and particularly because of the fact that substantially no current flows in the resistor 21 of the probe, so that the temperature of this probe is not raised but remains equal to the temperature of the ambient atmosphere in which it is required to perform its monitoring function.

By means of a probe the mean resistance of which is about $10^6$ ohms in the inoperative condition and about $10^3$ ohms in the presence of mist the electric circuit of the detector can be greatly simplified and limited to connecting the probe in series with a signalling glow-lamp and a suitable charge resistor, the assembly being fed by a low-voltage source which may supply a direct current or an alternating current. Manufacture of such a detector is particularly economical.

What is claimed is:

1. Probe for selectively detecting polar molecules in a gaseous mixture in contact with the probe, the operation of the probe being based on the variation of its electrical resistance due to a reaction at the probe surface, characterized in that it comprises a substrate on which is deposited a layer of a semiconductor material of thickness 0.05 to 0.08 $\mu$um to which are connected at least two electrodes and which is covered by a film of a dielectric material of thickness 0.01 to 0.04 $\mu$um at least part of which is active as a detection area.

2. Probe as claimed in claim 1, characterized in that the said semiconductor compound is zinc oxide.

3. Probe as claimed in claim 1, characterized in that the dielectric material is tetraethoxysilane.

4. Probe as claimed in claim 3 having continuous sensitivity, characterized in that the dielectric layer is polycondensed tetraethoxysilane.

5. Probe as claimed in claim 3 having threshold sensitivity, characterized in that the dielectric layer consists of polycondensed tetraethoxysilane covered by a monomolecular layer of monomeric tetraethoxysilane.

6. Probe as claimed in claim 1 for detecting humidity and having threshold sensitivity, characterized in that the dielectric material is polytetrafluoroethylene.

* * * * *

UNITED STATES PATENT AND TRADEMARK OFFICE
CERTIFICATE OF CORRECTION

PATENT NO. : 4025892

DATED : May 24, 1977

INVENTOR(S) : JEAN POMPEI ET AL

It is certified that error appears in the above-identified patent and that said Letters Patent are hereby corrected as shown below:

Claim 1, line 7, "μum" should be --μm--;

line 10, "μum" should be --μm--.

Signed and Sealed this

Thirteenth Day of September 197

[SEAL]

Attest:

RUTH C. MASON
*Attesting Officer*

LUTRELLE F. PARKER
*Acting Commissioner of Patents and Trademark*